United States Patent [19]

Boquet

[11] Patent Number: 5,344,543
[45] Date of Patent: Sep. 6, 1994

[54] METHOD OF MANUFACTURING A PLATE OF GELL FOR SEPARATING AND TRANSFERRING MACROMOLECULES BY ELECTROPHORESIS, AND PLATES OF GEL OBTAINED IN THIS WAY

[75] Inventor: Jean Boquet, Le Perray-en-Yvelines, France

[73] Assignee: Bertin & Cie, Plaisir, France

[21] Appl. No.: 937,898

[22] PCT Filed: Feb. 13, 1992

[86] PCT No.: PCT/FR92/00142

§ 371 Date: Oct. 13, 1992

§ 102(e) Date: Oct. 13, 1992

[87] PCT Pub. No.: WO92/14538

PCT Pub. Date: Sep. 3, 1992

[30] Foreign Application Priority Data

Feb. 14, 1991 [FR] France .................. 91 01734

[51] Int. Cl.⁵ .................................. C25B 9/00
[52] U.S. Cl. ...................... 204/299 R; 204/182.8; 436/178; 264/259
[58] Field of Search ............ 204/182.8, 299 R; 436/178; 264/259

[56] References Cited

U.S. PATENT DOCUMENTS 3,766,047 10/1973 Elevitch .................. 204/299 R
3,960,499 6/1976 White .................... 204/299 R
4,006,069 2/1977 Hiratsuka et al. ........... 204/182.8

FOREIGN PATENT DOCUMENTS 196790 10/1986 European Pat. Off. .
WO87/02132 4/1987 PCT Int'l Appl. .

Primary Examiner—John Niebling
Assistant Examiner—C. Delacroix-Muirheid
Attorney, Agent, or Firm—Bell, Seltzer, Park & Gibson

[57] ABSTRACT

A method of manufacturing a plate of gel for separating and transferring macromolecules by electrophoresis, the method consisting in fixing the periphery of a microporous membrane (10) to a frame (12) and in casting the liquid gel into the frame while avoiding any solid contact with the free face (24) of the membrane opposite to its face that is to be covered in gel, e.g. by placing the frame (12) on a slab (14), with the membrane (10) being above the frame and the slab, and then casting the gel into the frame (12) beneath the membrane (10).

8 Claims, 1 Drawing Sheet

METHOD OF MANUFACTURING A PLATE OF GELL FOR SEPARATING AND TRANSFERRING MACROMOLECULES BY ELECTROPHORESIS, AND PLATES OF GEL OBTAINED IN THIS WAY

BACKGROUND OF THE INVENTION

1. Field of the Invention

The invention relates to a method of manufacturing a plate of gel for separating and transferring macromolecules by electrophoresis, and also to plates of gel obtained by performing the method.

2. Description of the Prior Art

Such plates comprise a layer of gel, e.g. agarose or polyacrylamide, adhering to one face of a thin microporous membrane, e.g. made of nitrocellulose, "nylon", PVDF (polyvinylidene difluoride), or even special paper. Samples of macromolecules such as nucleic acids or proteins are deposited in wells formed in the layer of gel at one end of the plate, and the plate is then placed in a bath of appropriate liquid between electrodes of opposite polarities. Under the effect of the electric field between the electrodes, the macromolecules move longitudinally through the layer of gel at speeds that are a function of their molecular masses. At the end of a given length of time, they will have travelled lengths or distances that differ as a function of their molecular masses, and they can thus be separated from one another. They are then transferred through the thickness of the gel onto the membrane that adheres to the plate of gel, for the purpose of hybridizing and subsequent detection.

The plates of gel used in this known (so-called "Multi-Blotter") technique for separating and transferring macromolecules must satisfy a certain number of criteria, such as planeness of the membrane, constant thickness of the gel, uniformity of the gel, no bubbles of air in the gel or at the gel-membrane interface, and cleanness of the free face of the membrane opposite from its face covered with gel.

To manufacture such plates, it is possible to fix membranes around their peripheries to frames, and then to cast the gel while in a very liquid state into such frames in order to cover the membranes. The gel is then allowed to set. The gel naturally adheres quite strongly to the membranes and tends to fill the micropores in the membranes by capillarity.

When the membranes are placed on a plane surface for the gel to be cast, plates are obtained having membranes that are plane, but that leave traces of gel or that have gel of thickness that varies to a greater or lesser extent on the faces of the membranes opposite from the faces that are normally covered in gel. During casting, the very liquid gel penetrates into the membranes and passes through them so as to come into contact with the support surface where it accumulates to a greater or lesser extent. In addition, bubbles of air are often held captive between the membrane and the gel or within the gel.

In contrast, if support is provided only for the peripheral frames to which the membranes are fixed while the gel is being cast, then the membranes themselves are no longer supported by a plane surface, so their free faces remain clean, but the membranes become curved under the weight of the gel and take up a bulging shape that they retain once the gel has set.

To avoid those drawbacks, proposals have already been made to saturate the membranes with water before casting the gel and then to place them on a plane surface and to subject them to rolling in order to eliminate bubbles of air and make the membranes adhere to the plane surface. The gel is then cast on the membranes while they are resting on said plane surface. The water present in the micropores of the membranes prevents the gel from passing through the membranes, thereby ensuring that the faces of the membranes opposite to those that are covered with gel remain clean.

Nevertheless, that known method is very lengthy and fiddley to perform, and it does not enable plates of gel to be made quickly.

SUMMARY OF THE INVENTION

A particular object of the present invention is to avoid the various drawbacks of the known methods of the prior art.

The present invention provides a method of manufacturing plates of gel capable of satisfying the above-specified criteria while remaining simple and quick to implement.

The invention also provides plates of gel of the above-specified type which are of perfect quality and which are identical to one another.

To this end, the present invention provides a method of manufacturing a plate of gel for separating and transferring macromolecules by electrophoresis, said plate comprising a layer of gel adhering to a face of a microporous membrane, the method consisting in fixing the periphery of the membrane to a frame, in casting the gel while in the liquid state into the frame, and in allowing it to set, the method being characterized in that it consists, while casting the gel into the frame, in supporting the membrane by a fluid and avoiding any solid contact with the free face of the membrane opposite from its face that receives the gel, thereby not changing or disturbing the surface tension forces on said free face between the membrane and the gel filling the micropores of the membrane, and simultaneously ensuring planeness for the membrane until the gel sets.

The invention is based on the observation that the gel poured on one face of a membrane and impregnating the membrane throughout its thickness does not flow from the membrane when the free face thereof is not in contact with a solid object. The surface tension forces that provide adherence between the gel and the membrane are sufficient to prevent the gel from oozing over the free face of the membrane. This free face which is opposite from the face that is covered in gel thus remains perfectly clean.

In a first implementation of the invention, the method consists in placing the frame carrying the membrane upsidedown on a horizontal plane surface such that the membrane is then on top of the frame and at a distance from said plane surface, and in casting the gel in the liquid state beneath the membrane, inside the frame, until the free surface of the gel reaches a predetermined level where the gel is in contact with the bottom face of the membrane and supports it in a horizontal plane.

Under such conditions, it is the gel that supports the membrane and that ensures its planeness.

The above-mentioned level reached by the gel is advantageously determined by an overflow orifice, e.g. formed in means for delivering the gel to the inside of the frame.

It is thus possible to adjust the position of said level accurately, which position corresponds to good planeness of the membrane.

In another implementation, the method of the invention consists in supporting the membrane and its frame by a cushion of air having a uniform pressure field acting against the free face of the membrane, and in casting the liquid gel onto the membrane, inside the frame. The pressure field of the air cushion is adjusted so as to support the weight of the membrane, the weight of the frame, and the weight of the gel cast into the frame and on the membrane. The uniformity of the pressure field ensures excellent planeness for the membrane. The above-mentioned air cushion may be produced by means of a fluidized slab having a top wall that is porous or microperforated, and that is fed by a flow of air under pressure.

The invention also provides a plate of gel for separating and transferring macromolecules by electrophoresis, the plate comprising a layer of gel of constant thickness adhering to a face of microporous membrane, and being characterized in that the membrane is plane and in that the gel fills the micropores of the membrane without overflowing onto the free face of the membrane opposite from its face covered in gel.

According to another feature of the invention, the gel forms meniscuses that are concave in the pores that open out to said free face of the membrane.

Such gel plates have identical characteristics of gel thickness, of membrane planeness, and of membrane impregnation by the gel, and they enable macromolecules to be separated and transferred reproducibly and reliably.

The invention will be better understood and other characteristics, details and advantages thereof will appear more clearly on reading the following description given by way of example with reference to the accompanying drawing.

DESCRIPTION OF THE PREFERRED EMBODIMENTS

Figure 1:
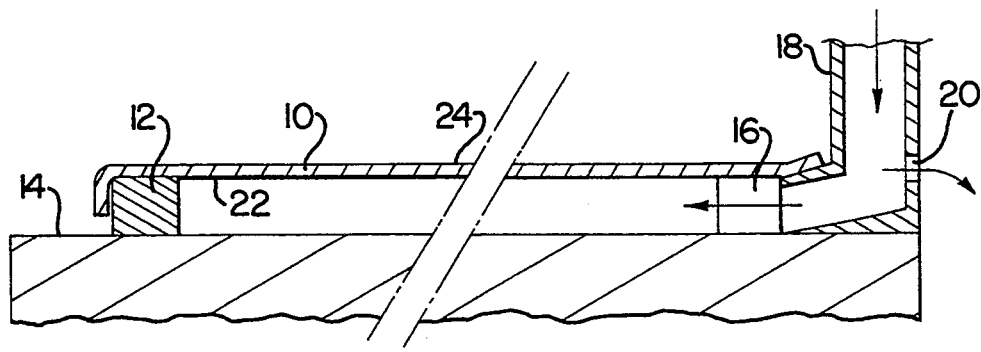
FIG. 1 is a diagram of a first implementation of the invention.

Reference is made initially to FIG. 1 which shows a first implementation of the invention.

In this figure, a microporous membrane 10, e.g. made of nitrocellulose, of "nylon", of PVDF, or of special paper, has its periphery fixed to a frame 12 whose height may be equal to the thickness of the layer of gel that is to be formed on the membrane. The frame is placed upsidedown on a support slab 14 having a perfectly plane top surface, such that the membrane 10 is on top of the frame and at a distance from the slab 14 that corresponds to the thickness of the frame.

The thickness of the membrane is 0.1 mm to 0.2 mm, for example, and its means pore size may be about 0.5 $\mu$m. The layer of gel to be formed on the membrane has a thickness of a few mm, for example.

The frame 12 which may be rectangular in shape, for example, has an outline that is continuous except for a zone 16 which is associated with an external duct 18 for delivering liquid gel. The bottom end of the duct 18 is connected in substantially sealed manner to the opening 16 of the frame 12, while its top end is connected to gel feed means.

A wall of the duct 18 includes an overflow orifice 20 whose bottom edge is at a level that corresponds exactly to the level desired for the bottom face 22 of the membrane which is to be covered in gel.

The method of the invention is very simple to implement.

It suffices to place the frame 12 carrying the membrane 10 on the slab 14 in the manner shown in FIG. 1, to connect its opening 16 to the bottom end of the duct 18, and to cast down the duct 18 the gel as liquefied, e.g. by heating to a temperature of about 55° C. (when it comprises agarose). The gel which is highly liquid at this temperature then fills the frame 12 with the free surface of the gel rising progressively inside the frame until it comes into contact with the bottom face 22 of the membrane and supports it in a plane that is accurately horizontal. As soon as the gel has reached this level inside the frame 12, excess gel delivered by the duct 18 flows away to the outside via the overflow orifice 20. Simultaneously, the gel impregnates the membrane 10 and fills the micropores thereof by capillarity.

The planeness of the membrane corresponds to the planeness of the free surface of the gel inside the frame 12 and it is perfect.

Proper positioning of the overflow orifice 20 makes it possible to avoid the membrane being slightly curved, either convexly or concavely, and prevents the gel passing through the membrane and overflowing onto the top face 24 thereof.

In addition, any bubbles of air that may be captured beneath the membrane are expelled to the outside thereof as the gel fills the micropores of the membrane by capillarity.

Optionally, when beginning to cast gel into the frame, the slab 14 may be tilted so that the duct 18 is at the highest point thereof, thus making it possible to degas the gel delivered into the frame 12 by allowing bubbles of air to escape upwards via the duct 18.

Figure 2:
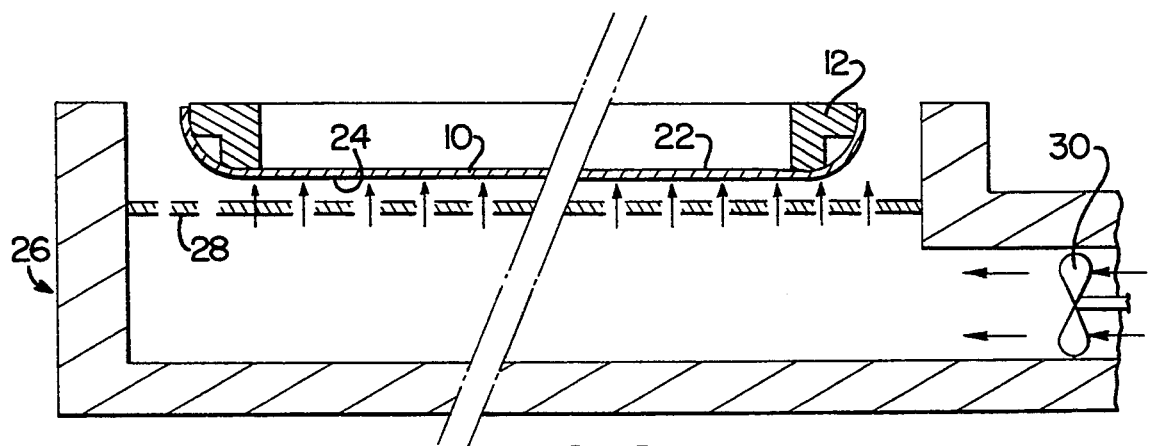
FIG. 2 is a diagram of a second implementation of the invention.

FIG. 2 shows a variant of the invention.

In this variant, a cushion of air having a uniform pressure field is used to support the membrane 10, with the periphery of the membrane being fixed to the frame 12, now disposed so that the membrane 10 is beneath the frame.

The supporting air cushion is produced by a fluidized slab 26 of conventional type whose top wall 28 has a top face that is perfectly horizontal and plane and is porous or microperforated to allow air to escape upwards as shown by the arrows. The slab is fed by a blower shown diagrammatically at 30 and which delivers air at a predetermined flow rate and pressure. The large head losses in the air on passing through the wall 28 ensure that uniform pressure is exerted on the free face 24 of the membrane opposite from its face 22 which is to receive the gel.

The wall 28 may be made of sintered material, for example, such as bronze or a composite material based on glass fibers.

While the slab 26 is being fed with air by the blower 30, the membrane and its frame may be disposed above the surface 28 and they are then supported in a stable manner by the cushion of air that forms between the membrane 10 and the surface 28. The liquid gel is then cast into the frame 12 until the layer of gel has the desired thickness (which may be the same as the thickness of the frame 12). The gel impregnates the membrane 10, but does not leave through the bottom face 24 thereof and it remains inside the micropores of the membrane.

The air feed to the slab 26 can be stopped as soon as the gel impregnating the membrane 10 has set.

As in the preceding embodiment, plates of gel are obtained having membranes that are perfectly plane, and in which the thickness of the layer of gel is constant. The gel impregnating the membrane expels the air contained in the micropores thereof.

Figure 3:
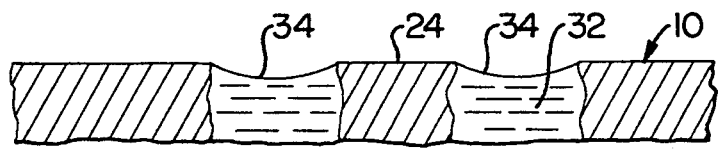
FIG. 3 is a highly diagrammatic view on a large scale of the free face of a membrane whose micropores are filled with gel.

In the majority of cases, plates of gel manufactured according to the invention present the following characteristic (shown diagrammatically in FIG. 3): the gel 32 fills the micropores of the membrane, and where said micropores open out into the face 24 of the membrane opposite from its face covered in gel, the gel forms meniscuses 34 that are concave because of the surface tension forces between the gel and the substance from which the membrane is made.

I claim:

1. A plate of gel for separating and transferring macromolecules by electrophoresis, the plate comprising a layer of gel of constant thickness adhering to a face of a microporous membrane, and being characterized in that the membrane is plane and in that the gel fills the micropores of the membrane without overflowing onto the free face of the membrane opposite from its face covered in gel.

2. A plate of gel according to claim 1, characterized in that the gel forms meniscuses that are concave in the pores that open out to said free face of the membrane.

3. A method of manufacturing a plate of gel for separating and transferring macromolecules by electrophoresis, said plate comprising a layer of gel adhering to a face of microporous membrane, the method comprising:

fixing the periphery of the membrane to a frame;

placing the frame carrying the membrane upside down on a horizontal plane surface such that the membrane is then on top of the frame and at distance from said plane surface equal to the thickness of the frame;

delivering the gel in a liquid state through a delivering means into the frame beneath the membrane, so that the membrane is supported by the gel;

avoiding any solid contact with the face of the membrane opposite from the face which adheres to the gel; and allowing the gel to set in contact with the membrane for adhering the membrane to the gel.

4. A method according to claim 3 wherein said gel is cast in a liquid state beneath the membrane until the surface of the gel reaches a predetermined level at which the gel is in contact with the bottom face of the membrane and supports it in a horizontal plane.

5. A method according to claim 4 wherein said predetermined level is determined by an overflow orifice formed in said delivering means.

6. A method of manufacture a plate of gel for separating and transferring macromolecules by electrophoresis, said plate comprising a layer of gel adhering to a face of a microporous membrane, the method comprising:

fixing the periphery of the membrane to a frame;

placing the frame with the membrane on an air cushion having a uniform pressure field, the membrane being below the frame so that the air cushion is acting against the membrane and supporting the membrane and the frame;

casting the gel in a liquid state onto the membrane, inside the frame;

avoiding any solid contact with the face of the membrane opposite from its face which receives the gel; and allowing the gel to set in contact with the membrane for adhering the membrane to the gel.

7. A method according to claim 6 wherein said cushion of air is provided by a means comprising a fluidized slab having a porous top wall with a top face that is plane and horizontal, said slab being fed with a flow of air under pressure.

8. The method according to claim 7 wherein said top wall is microperforated.

* * * * *

UNITED STATES PATENT AND TRADEMARK OFFICE
CERTIFICATE OF CORRECTION

PATENT NO. : 5,344,543
DATED : September 6, 1994
INVENTOR(S) : Jean Boquet

It is certified that error appears in the above-identified patent and that said Letters Patent is hereby corrected as shown below:

On the title page, item [54] and column 1, line 3, "Gell" should be --Gel--.

Column 2, line 45, after "flow" insert -- out --.

Column 3, line 63, "means" should be -- mean --.

Column 5, line 40, after "of" insert -- a --.

Column 5, line 44, after "at" insert -- a --.

Column 6, line 19, "manufacture" should be -- manufacturing --.

Signed and Sealed this

Fifteenth Day of November, 1994

Attest:

BRUCE LEHMAN

*Attesting Officer*  *Commissioner of Patents and Trademarks*